(12) United States Patent
Christ et al.

(10) Patent No.: US 8,906,639 B2
(45) Date of Patent: Dec. 9, 2014

(54) METHOD OF DETERMINING FACTOR XIII WITH THE AID OF PLASMA-BASED REFERENCE MATERIAL

(75) Inventors: Gerlinde Christ, Marburg (DE); Andreas Kappel, Koenigstein (DE); Lena Pechmann, Lohra (DE); Frank Vitzhum, Biedenkopf (DE); Norbert Zander, Marburg (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 0 days.

(21) Appl. No.: 13/498,923

(22) PCT Filed: Jun. 17, 2010

(86) PCT No.: PCT/EP2010/003667
§ 371 (c)(1),
(2), (4) Date: Mar. 29, 2012

(87) PCT Pub. No.: WO2011/042072
PCT Pub. Date: Apr. 14, 2011

(65) Prior Publication Data
US 2012/0190053 A1    Jul. 26, 2012

(30) Foreign Application Priority Data

Oct. 5, 2009   (DE) .................... 10 2009 048 199

(51) Int. Cl.
C12Q 1/56         (2006.01)
G01N 33/573     (2006.01)
G01N 33/86       (2006.01)

(52) U.S. Cl.
CPC ............ *G01N 33/86* (2013.01); *G01N 33/5735* (2013.01); *C12Q 1/56* (2013.01)
USPC ........................................ 435/13

(58) Field of Classification Search
USPC ............................................ 435/13
See application file for complete search history.

(56) References Cited

U.S. PATENT DOCUMENTS 5,204,240 A * 4/1993 Stuber ............................. 435/13

FOREIGN PATENT DOCUMENTS

EP        0314023        5/1989
EP        0456152        11/1991

OTHER PUBLICATIONS

Kappel et al., Haostaseologie, 2010, vol. 30(1), pp. A114, Nurenberg, Germany, Feb. 2010.*
Muszbek, L. et al., Kinetic Determination of Blood Coagulation Factor XIII in Plasma., Clin. Chem. 31(1): 35-40, (1985).
Lim, W. et al., Prophylactic and perioperative replacement therapy for acquired factor XIII deficiency, J. Thromb Haemost, 2: 1017-19, (2004).
Ajzner E. and Muszbek L., Prophylactic and perioperative replacement therapy for acquired factor XIII deficiency: a rebuttal, J. Thromb. Haemost, 2: 2075-2077, (2004)
International Search Report for PCT/EP2010/003667 dated Sep. 3, 2010.
Fickenscher, Karl et al., "A Photometric Assay for Blood Coagulation Factor XIII," Thrombosis and Haemostasis, vol. 65, No. 5, 6 pages 1991.
Karpati, Levente et al., "A Modified, Optimized Kinetic Photometric Assay for the Determination of Blood Coagulation Factor XIII Activity in Plasma," Clinical Chemistry, vol. 46, No. 12, 10 pages 2000.

* cited by examiner

*Primary Examiner* — Maryam Monshipouri
(74) *Attorney, Agent, or Firm* — King & Spalding L.L.P.

(57) ABSTRACT

The present invention is in the field of in-vitro diagnostics and relates to a method of determining the blood-clotting factor XIII (factor XIII, F XIII) with the aid of plasma-based reference material, and a test kit for carrying out the method.

5 Claims, 4 Drawing Sheets

METHOD OF DETERMINING FACTOR XIII WITH THE AID OF PLASMA-BASED REFERENCE MATERIAL

This application is the U.S. National Stage of International Patent Application No. PCT/EP2010/003667 filed on Jun. 17, 2010 and claims the benefit of German patent application no. 102009048199.0 filed on Oct. 5, 2009. All of the applications are incorporated by reference herewith in their entirely.

The present invention is in the field of in-vitro diagnostics and relates to a method of determining the blood-clotting factor XIII (factor XIII, F XIII) with the aid of plasma-based reference material, and a test kit for carrying out the method.

Factor XIII is a blood-clotting factor which acts at the end of the blood coagulation cascade and plays an important role in permanent wound closure. During the last phase of blood coagulation, i.e. fibrin formation, thrombin cleaves fibrinogen. The fibrin monomers formed in this manner aggregate spontaneously to form long fibers and finally a dense branched network of soluble fibrin polymers. Factor XIII, too, is activated by thrombin, resulting in the formation of factor XIIIa. Factor XIIIa causes crosslinking of the fibrin polymers, making the fibrin clot mechanically more stable, less deformable and more resistant to dissolution by plasmin. A congenital or acquired factor XIII deficiency may lead to a tendency to bleed, to would healing disturbances and to miscarriages. Owing to its clinical relevance, the determination of factor XIII for exclusion or confirmation of a factor XIII deficiency is an important component of coagulation diagnostics.

Factor XIIIa, the activated form of the catalytically inactive proenzyme factor XIII, is a transglutaminase which catalyzes three-dimensional crosslinking of the fibrin polymers by formation of intermolecular amide bonds between lysyl and glutaminyl amino acid side chains of the fibrin molecules. This reaction releases ammonia ($NH_3$) or ammonium ions ($NH_4^+$). Hereinbelow, for the sake of simplicity, the term ammonia is used both for ammonia and for ammonium ions. The phenomenon of ammonia formation is used in various tests to determine factor XIII:

Muszbek, L. et al. [Clin. Chem. (1985) 31(1), 35-40] describe a method to determine factor XIII in defibrinated plasma samples where the factor XIII of the sample is activated with thrombin to give factor XIIIa. Furthermore, the sample is mixed with β-casein and ethylamine which serve as substrates for the formation of intermolecular amide bonds by factor XIIIa. To detect the ammonia released in this reaction quantitatively, the sample is additionally mixed with NADPH (nicotinamide adenine dinucleotide phosphate hydride) and with components of an NADPH-dependent indicator reaction, namely glutamate dehydrogenase (GLDH) and α-ketoglutarate. In the presence of ammonia, GLDH converts α-ketoglutarate into glutamate. This reaction additionally consumes NADPH, and NADP+ (nicotinamide adenine dinucleotide phosphate), the oxidized form of NADPH, is formed. The absorption spectrum of NADP+ is different to that of NADPH, such that the absorption (extinction or optical density) of the test mixture changes in proportion to the consumption of NADPH and thus in proportion to the amount of ammonia and thus in proportion to the amount or activity of factor XIII. Alternatively, NADH may be used instead of NADPH in this test mixture. In contrast to NADP+, NADPH has, in addition to an absorption maximum at about 260 nm, an absorption maximum at about 340 nm. The exact position of absorption maxima generally depends on various parameters, in particular on the dielectric constant and the pH of the solution. In general, the absorption maximum of the NADPH is in the range from 335 to 345 nm. Accordingly, measuring the change in absorption of the test mixture usually at a wavelength of about 340±5 nm permits the quantitative determination of factor XIII in a sample.

EP 336 353 A2 or Fickenscher et al. (Thromb Haemost. 1991, 65(5): 535-40) describe a similar method where factor XIII is quantified by the ammonia released. EP 336 353 A2 describes a method for determining factor XIII in fibrin-containing plasma samples without any pretreatment. To suppress the formation of interfering fibrin clots in the reaction mixture, the sample is additionally mixed with a fibrin aggregation inhibitor. The factor XIII in the sample is activated with thrombin in the presence of $Ca^{2+}$ ions to factor XIIIa. Furthermore, the sample is mixed with a synthetic glutamine-containing peptide and glycine ethyl ester which serve as substrates for the formation of intermolecular amide bonds by factor XIIIa. To detect the ammonia released in this reaction quantitatively, the sample is additionally mixed with NADH (nicotinamide adenine dinucleotide hydride) and with components of an NADH-dependent indicator reaction, namely with glutamate dehydrogenase (GLDH) and α-ketoglutarate. In the presence of ammonia, GLDH converts α-ketoglutarate into glutamate. This reaction additionally consumes NADH, and NAD+, the oxidized form of NADH, is formed. The absorption spectrum of NAD+ is different to that of NADH, such that the absorption of the test mixture changes in proportion to the consumption of NADH and thus in proportion to the amount of ammonia and thus in proportion to the enzymatic activity of factor XIII and thus in proportion to the amount of factor XIII. Alternatively, NADPH may be used instead of NADH in this test mixture. By measuring the change in absorption of the test mixture at a wavelength of 340 nm, quantitative determination of factor XIII in a sample is possible. A commercial test based on the test principle described in EP 336 353 A2 is the Berichrom® F XIII test from Siemens Healthcare Diagnostics.

For the sake of simplicity, the term NAD(P)H is used when referring both to the phosphorylated and the non-phosphorylated form of NADH, i.e. when referring to NADH and likewise to NADPH. The term NAD(P)+ is used when reference is made both to the phosphorylated and the non-phosphorylated form of NADH in the oxidized state, i.e. when referring to NAD+ and likewise to NADP+.

Instead of NADH or NADPH, it is also possible to use analogs of NADH or NADPH, so-called NAD(P)H analogs, in the test methods described. Preference is given to analogs having an absorption maximum above 350 nm. An analog is a substance which mimics the biological action of the physiological substance, i.e. in the present case, for example, a substance which, like NAD(P)+ or NAD(P)H, may act as a cosubstrate. This has to be an analog where the oxidized and the reduced form have different absorption maxima and where the absorption maximum of the NAD(P)H analog is above 350 nm. Preference is given to using structural analogs where the nicotinamide group has been replaced for another group. Here, preference is given to cyclic compounds, in particular heterocyclic compounds, very especially preferably pyridine analogs, i.e., for example, 3-acetylpyridine, 3-(carb)aldehydepyridines, thionicotinamide, selenonicotinamide, etc.

The methods described above of the prior art and other methods for determining the factor XIII activity based on the detection of ammonia formation in the test mixture have the disadvantage that, in samples having low factor XIII concentrations, the factor XIII activity measured is frequently high. It has even been found that, in plasma samples of patients having a severe acquired factor XIII deficiency, where it was not possible to detect a factor XIII by immunological and other methods, the Berichrom® F XIII test detected a factor XIII activity of 8-14% (Lim, W. et al., J Thromb Haemost 2004; 2: 1017-1019). However, in particular in samples having low factor XIII concentrations, correct determination of the factor XIII activity is an essential precondition for the best possible therapeutic treatment of the patients with factor XIII concentrate.

The reason for the excessive values incorrectly found for the factor XIII activities is unknown. A possible cause that is being discussed is a factor XIIIa-independent NADH or NADPH consumption, possibly triggered by enzymes which are present in the sample from the patient and utilize NADH or NADPH as a cofactor, or by unspecific formation of ammonia in the sample from the patient, which would also result in a factor XIIIa-independent NADH or NADPH consumption (Ajzner, E and Muszbek, L.; J Thromb Haemost 2004; 2: 2075-2077). To solve the problem of the excessively high factor XIII activities found, Ajzner & Muszbek propose mixing a second aliquot of the sample from the patient in a parallel test with iodoacetamide and determining the factor XIII activity. Iodoacetamide inhibits the transglutaminase activity of activated factor XIII. The change in absorbance measured in this parallel test corresponds to the factor XIIIa-independent NADH or NADPH consumption which can then be subtracted from the activity measured in the regular test mixture not treated with iodoacetamide. In this manner, it is possible to correct the factor XIII activity measured in the regular test mixture.

However, this method of correcting the factor XIII activity has the disadvantage that every sample from a patient has to be measured twice, once without and once with iodoacetamide. Such an approach would double not only the number of samples to be tested, but also the costs of a factor XIII determination. Moreover, it is not clear whether the use of iodoacetamide is suitable for routine employment in coagulation analyzers.

Accordingly, is was an object of the present invention to provide means and methods for determining factor XIII which allow the correct determination of factor XIII in particular in plasma samples having a low factor XIII concentration or activity, without measuring a parallel test.

The object is achieved by using exclusively plasma as reference material for factor XIII activities of less than 100% of the norm.

In the known methods for determining factor XIII in plasma samples, the reference material used is usually a normal plasma pool, for example from the plasma of generally at least 20 apparently healthy donors. The factor XIII activity of this normal plasma is defined as 100% or as norm, or it is compared to that of the factor XIII activity of an international reference plasma, whereby a factor XIII activity value can be assigned to the normal plasma. To provide references having a lower factor XIII activity (<100%), dilutions of this normal plasma are prepared. The diluents used are usually aqueous solutions such as, for example, 0.9% strength NaCl solution. For example, one part of normal plasma is mixed with two parts of a suitable buffer (1:2 dilution) and defined as a reference having a factor XIII activity of 33.33% of the norm. By measuring the normal plasma and a number of dilutions of the normal plasma using the factor XIII test to be standardized, a reference curve (calibration curve) is constructed by assigning the defined factor XIII activities (for example in % of the norm) to the crude values measured. For samples from patients, the crude value can then be measured in the standardized test system and, using the reference curve, be converted finally into a calibrated value or a standardized test result, for example in % of the norm.

It has been found that by using references for the norm value of the factor XIII activity (100%) and for factor XIII activities below the norm value (<100%) which consist exclusively of plasma a reference curve is obtained which allows the correct determination of factor XIII, in particular in plasma samples having a low factor XIII concentration or activity, by means of a method where the transglutaminase activity of the activated factor XIIIa is measured via the consumption of NAD(P)H in the test mixture.

The present invention provides a method for the quantitative determination of factor XIII in a plasma sample, where the transglutaminase activity of the activated factor XIIIa is measured via the oxidative consumption of NAD(P)H in the test mixture and where the measured value determined is compared to reference values which are determined with the aid of reference materials, where at least the reference materials having a reduced factor XIII activity compared to the norm consist of plasma.

A method for the quantitative determination of factor XIII in a plasma sample where the transglutaminase activity of the activated factor XIIIa is measured via the oxidative consumption of NAD(P)H in the test mixture is to be understood as meaning, for example, a method where a plasma sample is mixed I. with a substance or a substance mixture for activating factor XIII to factor XIIIa,
II. with an acceptor substrate for factor XIIIa having at least one glutaminyl group,
III. with an amino group donor substrate for factor XIIIa,
IV. with NAD(P)H or an NAD(P)H analog and
V. with an agent capable of oxidizing NAD(P)H to NADP+ in the presence of ammonia, and the change in absorption of the test mixture is measured.

A substance suitable for activating factor XIII to factor XIIIa is in particular thrombin, for example of human or bovine origin or else recombinant thrombin, preferably in the presence of calcium ions. Likewise suitable are substances or substance mixtures such as, for example, factor Xa, the snake venom ecarin or a mixture of tissue factor, phospholipids and $Ca^{2+}$ ions which effect indirectly activation of factor XIII by directly or indirectly activating the prothrombin present in the sample to thrombin which then in turn activates factor XIII.

The term "acceptor substrate for factor XIIIa having at least one glutaminyl group" is to be understood as meaning a polypeptide or peptide mimetic having at least one glutaminyl group, for example from the amino acid glutamine. Known acceptor substrates for factor XIIIa are, for example, β-casein and a large number of synthetic peptides. Suitable synthetic peptides are described, for example, in EP 314 023 A2.

The term "amino group donor substrate for factor XIIIa" is to be understood as meaning in particular primary amines. Preferred primary amines are ethanolamine, putrescine, cadaverine, diaminoethane, aminoethane. Particularly preferred primary amines are glycine ethyl ester or glycine methyl ester.

The term "NADH" is the abbreviation for the compound nicotinamide adenine dinucleotide hydride. For the purpose of the present invention, NADH consumption is to be understood as meaning the oxidation of NADH to NAD+ (nicotinamide adenine dinucleotide). The term "NADH" is to be interpreted broadly and also comprises the following NADH analogs which can be oxidized in a manner analogous to NADH and which, in oxidized form, likewise have optical properties which differ from those of their reduced form, so that their consumption can be measured photometrically:

NADPH (nicotinamide adenine dinucleotide phosphate hydride, which can be oxidized to NADP+), thio-NADH (thionicotinamide adenine dinucleotide hydride, which can be oxidized to thio-NAD+), thio-NADPH (thionicotinamide adenine dinucleotide phosphate hydride, which can be oxidized to thio-NADP+), seleno-NADH (selenonicotinamide adenine dinucleotide hydride, which can be oxidized to seleno-NAD+) and seleno-NADPH (selenonicotinamide adenine dinucleotide phosphate hydride, which can be oxidized to seleno-NADP+). When using NADH or NADPH, the change in absorbance owing to the oxidation to NAD+ or NADP+ is measured at a wavelength of about 340 nm. When using thio-NADH, thio-NADPH, seleno-NADH or seleno-NADPH, the change in absorbance owing to the oxidation to thio-NAD+, thio-NADP+, seleno-NAD+ or seleno-NADP+ is measured at wavelengths of about 340 nm to about 430 nm.

An "agent capable of oxidizing NADH to NAD+ in the presence of ammonia" is preferably an enzyme/substrate system which comprises an enzyme and a substrate for the enzyme, where the enzyme acts catalytically on the substrate and thereby oxidizes NADH to NAD+ or the NADH analogs mentioned above in the presence of ammonia.

Suitable enzyme/substrate systems are, for example, the glutamate dehydrogenase/ketoglutarate system or the alanine dehydrogenase/pyruvate system or the serine 2-dehydrogenase/3-hydroxypyrovate system or the valine dehydrogenase/3-methyl-2-oxobutanoate system or the leucine dehydrogenase/4-methyl-2-oxopentanoate system or the glycine dehydrogenase/glyoxylate system or the lysine dehydrogenase/1,2-didehydropiperidine-2-carboxylate system or the phenylalanine/phenylpyruvate system or the aspartate dehydrogenase/oxaloacetate system or the glucose-6-phosphate dehydrogenase/D-glucono-1,5-lactone-6-phosphate system.

In a preferred embodiment of the process according to the invention, the plasma sample is additionally mixed with a fibrin aggregation inhibitor. Fibrin aggregation inhibitors are substances which prevent the aggregation of thrombin-induced fibrin monomers. In this manner, the formation of a fibrin clot in a fibrinogen-containing sample, which would otherwise negatively affect the measurement of the absorption of the test mixture, is prevented. Preferred fibrin aggregation inhibitors are synthetic peptides such as, for example, a peptide of the sequence Gly-Pro-Arg-Pro (commercially available as Pefabloc®FG, Pentapharm, Switzerland). Other preferred peptides which can be used as fibrin aggregation inhibitors, in particular the preferred peptide of the sequence Gly-Pro-Arg-Pro-Ala, are described in EP 456 152 A2.

In a further embodiment, the sample is additionally mixed with a heparin-neutralizing substance, for example with hexadimethrine bromide (also known as Polybrene®) to eliminate the thrombin-inhibiting action of heparin which may be present, for example, in samples from patients undergoing heparin therapy.

Components I to V which are mixed with the sample to give a test mixture can each be mixed separately, i.e. in the form of individual reagents and in succession, with the sample; however, they can also be combined in a single reagent which is mixed with the sample in a single pipetting step. The reagent or the reagents preferably comprise a buffer matrix in which the substances are dissolved. A suitable buffer matrix contains, for example, HEPES, bicine, NaCl, albumin and/or preservatives such as, for example, sodium azide, and it has preferably a pH of from 6.0 to 9.0, particularly preferably from 6.5 to 8.5. Since calcium ions are required for the activation of F XIII, the buffer matrix furthermore comprises a calcium salt, preferably calcium chloride. Mixing of the reagent or the reagents with the sample may be carried out manually or using automatic instruments for measuring coagulation.

If the glutamate dehydrogenase/ketoglutarate system is used in the method according to the invention as the agent capable of oxidizing NADH to NAD in the presence of ammonia, the amount of glutamate dehydrogenase added to the test mixture is chosen such that the final concentration in the test mixture is 10-500 IU/ml, preferably 40-240 IU/ml.

A suitable sample material is in particular fibrinogen-containing plasma. However, according to the method according to the invention it is also possible to determine factor XIII in defibrinated plasma.

The change in absorption ($\Delta A$) of the test mixture is measured with the aid of a photometer comprising a light source, which sends a beam of light through the test mixture to be measured, and a detector, which measures the intensity of the light which has passed through and converts it into an electrical signal. Depending on whether NADH or NADPH or thio-NADH, thio-NADPH, seleno-NADH or seleno-NADPH is used, the change in absorption is measured using light of a wavelength of about 340 nm to about 430 nm. The changing absorption as a function of time correlates with the factor XIII activity. The decrease in absorption (A) of the test mixture owing to the consumption of the NADH or NADH analog is, in particular in the linear range of the reaction kinetics, directly proportional to the factor XIII activity.

Initially, the measured value determined for a plasma sample is a crude value. This value is then compared to reference values determined with the aid of reference materials. For the purpose of the present invention, a reference material is to be understood as meaning a material whose factor XIII concentration or activity is known.

In accordance with the present invention, at least the reference materials having a reduced factor XIII activity compared to the norm (<100% of the norm) consist of plasma. The term "plasma" is to be understood as meaning the liquid cell-free portion of blood of one or more donors, preferably human donors, obtained—as is customary in coagulation analysis—by removing the cellular blood components from anticoagulated whole blood. To suppress blood coagulation in a sample of whole blood, each blood sample—frequently even during the withdrawal of the blood—is mixed with an anticoagulant, preferably with a sodium citrate solution. Other customary anticoagulants are sodium heparin, lithium heparin, EDTA or citrate phosphate dextrose (CPD). Thus, every plasma necessarily comprises a certain portion by volume of anticoagulant.

A mixture of plasmas of a plurality of apparently healthy donors (plasma pool) is referred to as normal plasma. By definition, a normal plasma has a factor XIII concentration and thus a factor XIII activity of 100%. A factor XIII-deficient plasma is a plasma which has no, or at least not more than 1% of the normal, factor XIII activity. Factor XIII-deficient plasma can be obtained, for example, from patients having a corresponding phenotype or by selective immunoadsorption of factor XIII from a normal plasma by means of specific antibodies. For the sake of completeness, it should be mentioned that the actual factor XIII activity of different normal plasmas varies depending on manufacturer, batch, filling, etc. The actual factor XIII activity of a normal plasma is determined by the comparison with an international standard plasma for F XIII. The actual factor XIII activity of a normal plasma is generally between 80% and 120% of the international standard plasma.

A reference material according to the invention whose factor XIII activity is reduced compared to the norm may consist of a mixture of normal plasma and factor XIII-deficient plasma. To this end, normal plasma is mixed with a factor XIII-deficient plasma in such portions that the mixture obtained has the desired factor XIII activity. If, for example, one part of normal plasma is mixed with two parts of a factor XIII-deficient plasma (1:2 dilution), a reference material having a factor XIII activity of 33.33% of the norm is obtained. A reference material according to the invention which has a reduced factor XIII activity compared to the norm may furthermore consist of a factor XIII-deficient plasma to which purified, i.e. isolated factor XIII has been added in such an amount that a desired factor XIII activity is obtained. Human, animal or recombinant factor XIII is suitable. A reference material according to the invention having no factor XIII activity (≤1%) preferably consists of factor XIII-deficient plasma.

According to the invention, only reference materials consisting of plasma are used for determining the reference values or for constructing the reference curve for factor XIII activities below the norm value (<100%). In a preferred embodiment, a reference material which consists of normal plasma is used to determine the reference value for a factor XIII activity corresponding to the norm value (100%). In an embodiment which is likewise preferred, reference materials consisting of normal plasma to which isolated factor XIII has been added in such an amount that a desired factor XIII activity above the norm value is obtained are used to determine the reference values or to construct the reference curve for factor XIII activities above the norm value (>100%).

The present invention furthermore provides the use of factor XIII-deficient plasma for preparing reference material suitable for carrying out a method for the quantitative determination of factor XIII. As already described, the factor XIII-deficient plasma can be used as dilution medium for normal plasma, to thus prepare reference materials which consist of plasma and have a factor XIII activity below the norm value (<100%). However, the factor XIII-deficient plasma can also be used as matrix to which purified, i.e. isolated factor XIII is added in such an amount that a reference material is formed which has a desired factor XIII activity below or above the norm value.

The present invention furthermore provides a reference material having a factor XIII activity which is reduced compared to the norm (<100%) and which consists of a mixture of normal plasma and factor XIII-deficient plasma or which consists of a factor XIII-deficient plasma to which purified, i.e. isolated factor XIII has been added in such an amount that it has a factor XIII activity below the norm value. A reference material according to the invention can be provided in liquid or in lyophilized form.

The present invention furthermore provides a kit which comprises a normal plasma as a separate unit and a factor XIII-deficient plasma as a separate unit, in each case in liquid or in lyophilized form. With the aid of the normal plasma, it is possible to determine the reference value for the norm value of the factor XIII activity (100%). With the aid of the factor XIII-deficient plasma it is possible to determine the reference value for a missing factor XIII activity (0%). With the aid of mixtures of the two plasmas, which can be prepared by the user as desired, it is possible to determine reference values for any factor XIII activity lower than the norm (<100%).

The present invention furthermore provides a kit which comprises at least one reference material as a separate unit in liquid or lyophilized form which has a factor XIII activity lower than the norm (<100%) and consists of plasma, preferably of a mixture of normal plasma and factor XIII-deficient plasma. Preferably, a test kit according to the invention furthermore comprises a normal plasma as a separate unit and/or a factor XIII-deficient plasma as a separate unit.

EXAMPLES

Example 1

Determination of Factor XIII

Figure 1:
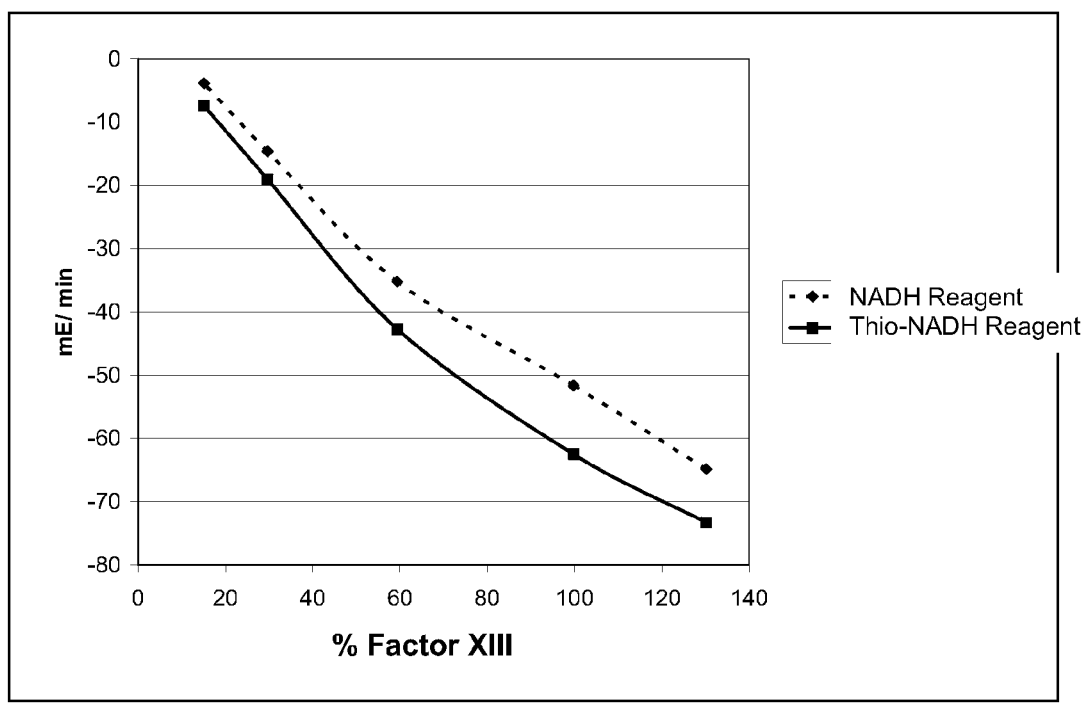
FIG. 1
Calibration curves for the NADH-based Berichrom® factor XIII test or the thio-NADH-based factor XIII test according to the prior art using NaCl solution as dilution medium for the standard plasma.

In the example below, the factor XIII content of plasma samples was determined using reagents comprising either NADH or thio-NADH as active component. The composition of the NADH-based reagent is described in EP 336 353 A2 or Fickenscher et al. (Thromb Haemost. 1991, 65(5): 535-40) and is commercially available from Siemens Healthcare Diagnostics (Germany) as Berichrom® factor XIII reagent. The thio-NADH-based reagent has the following composition:

Activator Reagent (pH 8.3):
    292 µM thio-NADH (Oriental Yeast Company, Rotterdam, The Netherlands)
    bovine thrombin (10 IU/ml)
    Gly-Pro-Arg-Pro-Ala-amide as fibrin aggregation inhibitor (2 g/l)
    calcium chloride (1.2 g/l)
    hexadimethrine bromide (10 mg/l)
    bovine albumin
    bicine buffer (100 mmol/l)

Detection Reagent (pH 6.5):
    glutamate dehydrogenase (160 U/ml)
    Leu-Gly-Pro-Gly-Gln-Ser-Lys-Val-Ile-Gly-amide as F XIII acceptor substrate (2.4 g/l)
    ADP
    glycine ethyl ester (1.4 g/l)
    α-ketoglutarate (2.7 g/l)
    bovine albumin
    HEPES buffer (10 mmol/l)

For the tests, of the respective reagents 75 µl of activator reagent, 75 µl of detection reagent and 15 µl of a plasma sample were combined in a cuvette on the BCS® XP coagulation analyzer (Siemens Healthcare Diagnostics Products GmbH, Marburg, Germany) and incubated at 37° C. After 5 minutes, the measurement of the absorbance was started. Test mixtures with the NADH reagent of the Berichrom® factor XIII test were measured using light of a wavelength of 340 nm. Test mixtures with the thio-NADH reagent were measured using light of a wavelength of 405 nm. For evaluation, the change of the absorbance per minute was calculated for a time window of 60 seconds—350 seconds after the start of the measurement. For calibration, i.e. to determine reference values, normal plasma (human standard plasma, Siemens Healthcare Diagnostics Products GmbH, Marburg, Germany) with a factor XIII concentration of 100% of the norm was used as standard (compared to the international standard for F XIII, this normal plasma contains 95% F XIII). Calibration points having a lower factor XIII concentration, i.e. reference values representing a factor XIII activity lower than the norm, were obtained according to the invention by diluting the standard with factor XIII-deficient plasma or, according to the prior art, by diluting the standard with 0.9% NaCl solution. Factor XIII-deficient plasma was obtained from Innovative Research (USA) or prepared using monoclonal antibodies against the alpha- or beta-chains of factor XIII analogously to the process described in EP 826 965 A1. Calibration points having a higher factor XIII concentration than that of the standard, i.e. reference values representing a factor XIII activity higher than the norm, were obtained by using an increased volume of the standard plasma in the test mixture.

Figure 2:
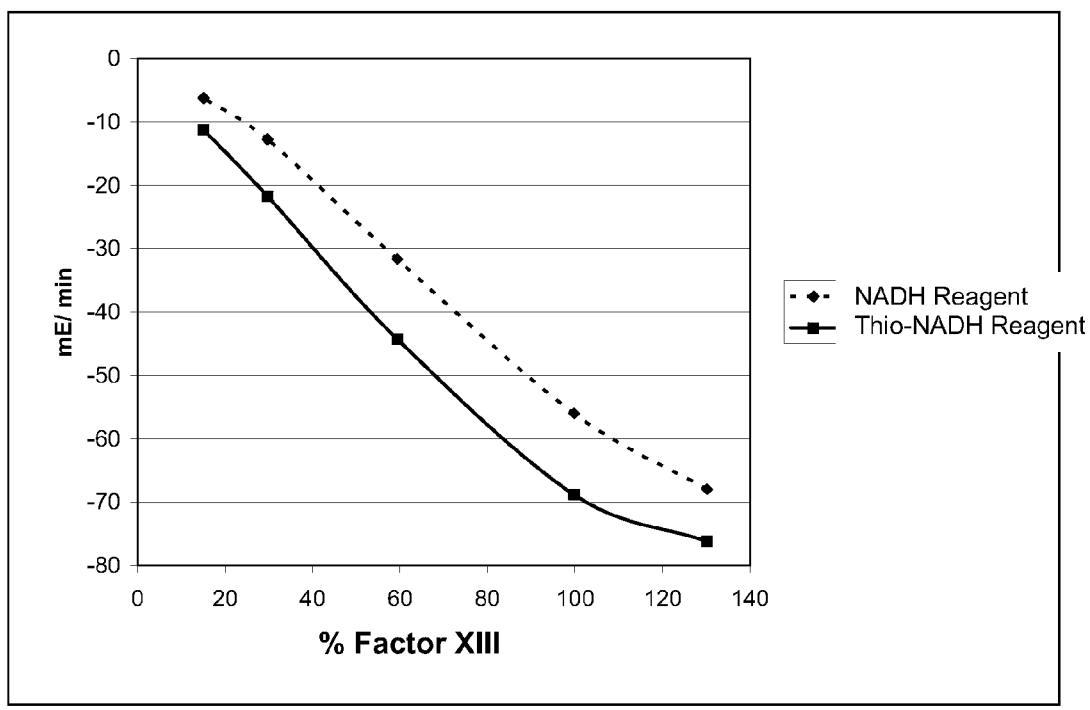
FIG. 2
Calibration curves for the NADH-based Berichrom® factor XIII test or the thio-NADH-based factor XIII test according to the invention using factor XIII-deficient plasma as dilution medium for the standard plasma.

Typical calibration curves for the tests carried out with the two reagents using NaCl solution as dilution medium are shown in FIG. 1. Typical calibration curves for the tests carried out according to the invention with the two reagents using factor XIII-deficient plasma as dilution medium are shown in FIG. 2.

Figure 3:
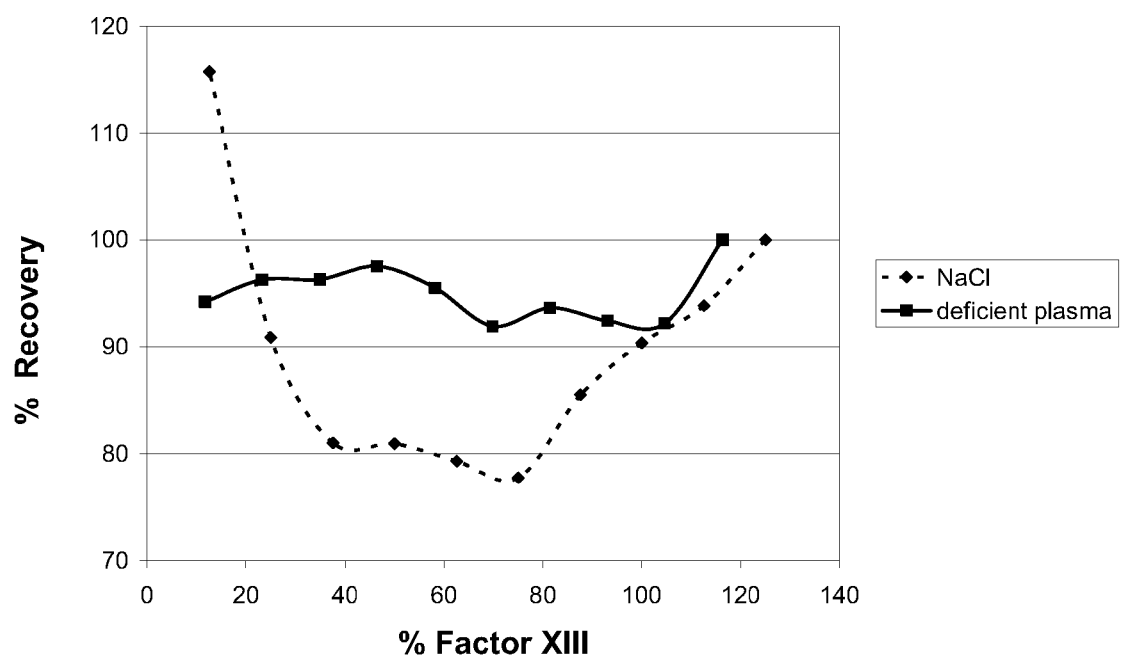
FIG. 3
Comparison of the recovery of samples of different factor XIII activity with the aid of the NADH-based Berichrom® factor XIII test carried out using NaCl or factor XIII-deficient plasma as dilution medium for the standard plasma.
Figure 4:
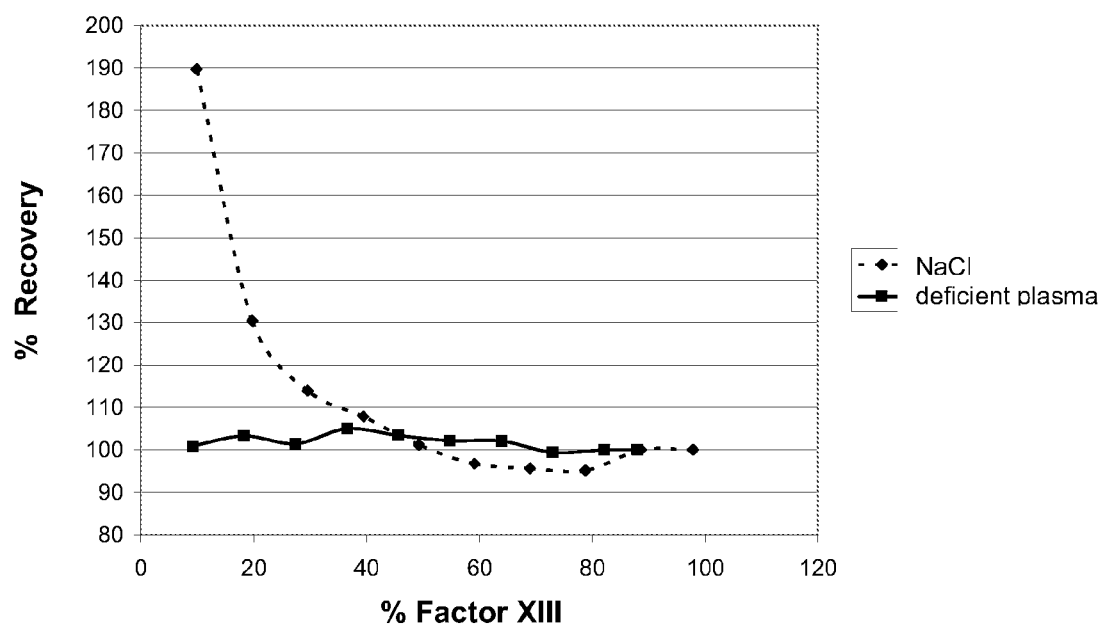
FIG. 4
Comparison of the recovery of samples of different factor XIII activity with the aid of the thio-NADH-based factor XIII test carried out using NaCl or factor XIII-deficient as dilution medium for the standard plasma.

Using the two reagents, samples having different factor XIII content were then measured, and the test results were evaluated using the respective calibration curves. The samples were prepared by mixing a plasma pool having a known high factor XIII activity with a factor XIII-deficient plasma in various ratios. The theoretical factor XIII activity value of each sample was calculated from the factor XIII activity values of the starting plasmas and the mixing ratio. After the measurement of the samples, the recovery in percent of each sample was calculated by comparison of the measured values actually determined and the factor XIII activity values calculated theoretically beforehand. A recovery of more than 100% is equivalent to a test result that is too high. As shown in FIG. 3, for the NADH-based Berichrom® factor XIII test the recovery in the case of samples having a factor XIII activity of less than 20% was closer to 100% when, according to the invention, factor XIII-deficient plasma was used as dilution medium for the standard instead of the NaCl required for the test. As shown in FIG. 4, for the thio-NADH-based test the improvement in the recovery of samples having a low factor XIII content is even more pronounced.

The invention claimed is:

1. A method for the quantitative determination of factor XIII content in a plasma sample, comprising:
    mixing the plasma sample with a substance or substance mixture for activating fact XIII to factor XIIIa,
    measuring the transglutaminase activity of the activated factor XIIIa via the oxidative consumption of an NAD(P)H analog in the test mixture, wherein the NAD(P)H analog is thio-NAD(P)H or seleno-NAD(P)H,
    determining one or more reference values for factor XIIIa activity using one or more reference materials having a reduced factor XIIIa activity compared to the norm value of 100%, wherein each of such one or more reference materials consists of plasma, and
    comparing the measured transglutaminase activity of the activated factor XIIIa in the plasma sample to at least the one or more reference values determined from the one or more reference materials having the reduced factor XIIIa activity compared to the norm value of 100% to determine the factor XIII content in the plasma sample.

2. The method of claim 1, where at least one of the reference materials having a reduced factor XIIIa activity compared to the norm value of 100% consists of a mixture of normal plasma and factor XIII-deficient plasma.

3. The method of claim 1, where at least one of the reference materials having a reduced factor XIIIa activity compared to the norm value of 100% consists of factor XIII-deficient plasma with added isolated factor XIII.

4. The method of claim 1, further comprising comparing the measured transglutaminase activity of the activated factor XIIIa in the plasma sample to a reference value determined from a reference material consisting of normal plasma.

5. The method of claim 1, further comprising comparing the measured transglutaminase activity of the activated factor XIIIa in the plasma sample to at least one reference value determined from at least one reference material having a factor XIIIa activity higher than the norm value of 100%, wherein each reference material having a factor XIIIa activity higher than the norm value of 100% consists of normal plasma with added isolated factor XIII.

\* \* \* \* \*